United States Patent
Damak et al.

(10) Patent No.: US 12,109,220 B2
(45) Date of Patent: *Oct. 8, 2024

(54) COMPOSITIONS FOR USE IN THE REDUCTION OF NOCICEPTION IN CHILDREN

(71) Applicant: SOCIETE DES PRODUITS NESTLE S.A., Vevey (CH)

(72) Inventors: Sami Damak, Lausanne (CH); Norbert Sprenger, Savigny (CH); Francis Foata, La Conversion (CH)

(73) Assignee: Societe des Produits Nestle S.A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 17/747,106

(22) Filed: May 18, 2022

(65) Prior Publication Data

US 2022/0331347 A1 Oct. 20, 2022

Related U.S. Application Data

(63) Continuation of application No. 16/956,723, filed as application No. PCT/EP2018/085862 on Dec. 19, 2018, now Pat. No. 11,357,785.

(30) Foreign Application Priority Data

Dec. 22, 2017 (EP) .................................. 17209905

(51) Int. Cl.
*A61K 31/702* (2006.01)
*A61K 9/00* (2006.01)
*A61K 31/7016* (2006.01)
*A61P 29/00* (2006.01)

(52) U.S. Cl.
CPC .......... *A61K 31/702* (2013.01); *A61K 9/0056* (2013.01); *A61K 9/0095* (2013.01); *A61K 31/7016* (2013.01); *A61P 29/00* (2018.01)

(58) Field of Classification Search
CPC .............. A61K 31/702; A61K 31/7016; A61K 9/0056; A61K 9/0095; A61P 29/00
See application file for complete search history.

(56) References Cited

U.S. PATENT DOCUMENTS

| 2013/0251844 A1 | 9/2013 | Sprenger et al. |
| 2016/0243139 A1* | 8/2016 | Vigsnæs ............ A61K 31/7004 |
| 2016/0296541 A1 | 10/2016 | Sangild |

FOREIGN PATENT DOCUMENTS

| RU | 2009116836 | 11/2010 |
| WO | 2016066175 | 5/2016 |
| WO | 2016139333 | 9/2016 |
| WO | 2017103019 | 6/2017 |

OTHER PUBLICATIONS

Aich et al., Int. J. Mol. Sci. 2015, 16, p. 29069-29092. (Year: 2015).*
Thongaram, T., Probiotic Metabolism of Human Milk Oligosaccharides (HMOs) and Prebiotics, 2014, doctoral thesis, University of Illinois at Urbana-Champaign, 144 pages. (Year: 2014).*
Russia Patent Office Communication for Application No. 2020123416/10, dated Apr. 8, 2022, 14 pages.
Hennet et al., Swiss Medical Weekly, 2014, 144, w13927, 9 pages. (Year: 2014).
Saavedra et al., Am. J. Clin. Nutr., 2004, 79, p. 261-267. (Year: 2004).
Brand et al., Neuropsychobiology, 2011, 64, p. 15-23. (Year: 2011).
Foata et al., "Activation of the G-protein Coupled Receptor GPR35 by Human Milk Oligosaccharides through different Pathways", Scientific Reports, vol. 10, Issue No. 01, Sep. 30, 2020, pp. 1-9.
European Office Action for Appl No. 18 819 152.2-1105 dated Jan. 5, 2024.
Loeser et al., "The Kyoto Protocol of IASP Basic Pain Terminology", Pain, vol. 137, Issue No. 3, 2008, pp. 473-477.
Chinese Office Action for Appl No. 201880078252.2 dated Oct. 17, 2023.

* cited by examiner

*Primary Examiner* — Jonathan S Lau
(74) *Attorney, Agent, or Firm* — K&L Gates LLP

(57) ABSTRACT

Compositions contain 6'-sialyllactose (6' SL) and lacto-N-tetraose (LNT), for use in the reduction of nociception in an infant or in a young child. The compositions are in particular useful in reducing abdominal pain, such as pain associated with infantile colic, irritable bowel syndrome (IBS) and/or recurrent abdominal pain (RAP), and consequently also contribute to reducing the crying periods and to improving the quality of sleep and the general quality of life of the infants and young children.

19 Claims, 7 Drawing Sheets

COMPOSITIONS FOR USE IN THE REDUCTION OF NOCICEPTION IN CHILDREN

CROSS REFERENCE TO RELATED APPLICATIONS

The present application is a continuation of U.S. patent application Ser. No. 16/956,723 filed Jun. 22, 2020, which is a National Stage of International Application No. PCT/EP2018/085862 filed Dec. 19, 2018, which claims priority to European Patent Application No. 17209905.3 filed on Dec. 22, 2017, the entire contents of which are being incorporated herein by reference.

FIELD OF THE INVENTION

The present invention relates to compositions comprising 6'-sialyllactose (6' SL) and lacto-N-tetraose (LNT), for use in the reduction of nociception in an infant or in a young child. The compositions are in particular useful in reducing abdominal pain, such as pain associated with intestinal discomfort and/or intestinal disorders, and consequently also contribute to reducing the crying periods and to improving the quality of sleep and the general quality of life of the infants and young children.

BACKGROUND

Infants, including newborn babies experience pain in the same was as adults, as revealed for example in Goksan et al.; *fMRI reveals neural activity overlap between adult and infant pain*; eLife 2015; 4:e06356. Other studies even suggest that infants could perceive pain more acutely than adults and older children.

Infants and young children can experience diverse types of pain, from acute pain to established pain, which could for example be caused by inflammation that may become chronic. In infants and young children, like in adults, pain is associated with reactions such as increased heart rate, faster and shallower respirations leading to lower oxygen saturation, and higher arterial pressure. Such reactions caused by prolonged or repeated exposure to pain have been found to have a negative impact on the development of infants and young children and may lead for example to abnormal development of the pain system such as hyperalgesia or to impaired regulation of stress-related hormones, such as increased production of cortisol. See for example Ziraldo, Breanne, "Infant Pain Management" (2010); *Senior Honors Theses;* 198, which can be obtained from Liberty University, Virginia, USA and is available at the date of filing under http://digitalcommons.liberty.edu/honors/198.

Infants and young children are particularly exposed to specific sources of pain, such as abdominal pain. Causes of abdominal pain include abdominal discomfort and abdominal disorders. One example of a common cause of discomfort is for example colic. The cause of colic is not completely understood but it seems related to gut hypersensitivity to pain, so that gut distension caused by the normal passage of gas or feces leads to pain in colicky infants, causing extensive crying periods, poor sleep and reduced quality of life for both the infant and the parents. Abdominal pain may also result from other causes of discomfort such as impaired stool patterns, exposure to new food, bloating and cramps. Disorders also occur, such as inflammatory bowel disease (IBD), diarrhea, e.g. infectious diarrhea, necrotizing enterocolitis (NEC) and functional abdominal pain disorders. Inflammatory bowel disease (IBD) is a serious chronic and destructive disorder of the gastrointestinal tract. It includes Crohn disease (CD) and ulcerative colitis (UC). Functional abdominal pain disorders and non-destructive disorders of the gastrointestinal tract and include irritable bowel syndrome (IBS), abdominal migraine and functional abdominal pain—not otherwise specified (FAP-NOS). A further detailed definition of functional abdominal pain disorders is provided in Hyams et al.; Childhood Functional Gastrointestinal Disorders: Child/Adolescent; Gastroenterology 150 (2016):1456-1468.

It is therefore desirable to reduce nociception in infants and young children. However, side effects associated with pain management medicines may be even more problematic in infants and young children than in adults. It would therefore be of particular interest to identify means of reducing nociception in infants and young children that are non-pharmacological and associated with low risk for the infant or young child. It would also be particularly advantageous to identify ingredients specially adapted to human infants and/or young children and capable of reducing nociception.

Mother's milk is recommended for all infants. However, in some cases breast feeding is inadequate or unsuccessful for medical reasons or the mother chooses not to breast feed. Infant formulae have been developed for these situations. Fortifiers have also been developed to enrich mother's milk or infant formula with specific ingredients. In such cases, it would be even more preferred to provide means to reduce nociception and thus to reduce the incidence of pain in infants and young children through nutritional intervention.

The effect of nutritional ingredients, such as human milk oligosaccharides on pain has already been investigated in the prior art. US2016/0243139 discloses the use of synthetic compositions containing one or more human milk mono- or oligosaccharides for treating visceral pain. According to the teaching of this document, a large variety of human milk mono- and oligosaccharides can be used, the preferred ones being 2'-FL, 3'FL, DFL, LNnT, 3'-SL, 6'-SL or LNFP-1 and the most preferred ones being a mix of 2'-FL and LNnT or LNT.

WO2016/139329 relates to compositions for use in improving stool consistency or frequency in infants or young children, such effects being associated with prevention and/or treatment of colic and/or gut discomfort. For this benefit, a nutritional composition comprising at least one fucosylated oligosaccharide and at least one N-acetylated oligosaccharide is used. The fucosylated oligosaccharide and the N-acetylated oligosaccharide may be selecting within a broad list. Most preferred fucosylated oligosaccharide is 2-FL and most preferred N-acetylated oligosaccharide is LNnT.

It would be useful to further optimize the effect of nutritional compositions on reduction of nociception in all infants and children.

Some specific populations of infants and young children are particularly in need of compositions able to reduce perception of pain. Such infants and young children are for example preterm infants, low birth weight infant, and/or growth-retarded infants or young children. Indeed such infants are often experiencing adverse medical conditions and require significantly more frequent medical intervention than term infants and infants having experienced normal development. Many of such medical interventions are unfortunately painful for the infant or young child, which is thus faced with repeated and sometimes acute pain. For such infants it is particularly advantageous to complement pharmacological pain management with nutritional compositions capable of reducing nociception.

There is clearly a need for developing suitable methods to reduce nociception in infants and young children.

There is also a need to deliver such health benefits in a manner that is particularly suitable for the young subjects (infants and young children), in a manner that does not involve a classical pharmaceutical intervention, as these infants or young children are particularly fragile.

There is a need to deliver such health benefits in these infants or young children in a manner that does not induce side effects and/or in a manner that is easy to deliver, and well accepted by the parents or health care practitioners.

There is also a need to deliver such benefits in a manner that does keep the cost of such delivery reasonable and affordable by most.

There is thus clearly a need to develop alternative methods than the classical pharmaceutical intervention such as the use of pharmaceutical analgesics, at least because of the associated risk of side effects.

SUMMARY

The present inventors have found that a composition comprising 6'-sialyllactose (6' SL) and lacto-N-tetraose (LNT) can advantageously be used to reduce nociception in an infant or a young child. Without wishing to be bound by theory it is believed that these oligosaccharides act synergistically to achieve this benefit, by activation of the G-protein coupled receptor 35 (GPR35). 6' SL and LNT have been found to be able to trigger activation of the GPR35 receptor individually and to synergistically trigger the activation of such receptor when used in combination. In contrast, unlike what would be suggested by the prior art, other human milk oligosaccharide (such as 3'-sialyllactose (3-SL), lacto-N-neotetraose (LNnT), 2'-fucosyllactose (2-FL) and difucosyllactose) do not activate the GPR35 receptor.

The receptor GPR35, which is highly expressed for example in the gastrointestinal tract, has been identified in numerous studies as being involved in the reduction of nociception and its activation has been described as causing analgesia (see for example Resta et al.; *Kynurenic acid and zaprinast induce analgesia by modulating HCN channels through GPR35 activation*; Neuropharmacology 108 (2016), 136-143; Cosi et al.; *G-protein coupled receptor 35 (GPR35) activation and inflammatory pain: Studies on the antinociceptive effect of kynurenic acid and zaprinast*, Neuropharmacology 60 (2011), 1227-1231; and Zhao et al.; *Targetting of the Orphan Receptor GPR35 by Pamoic Acid: A Potent Activator of Extracellular Signal-Regulated Kinase and 0-Arrestin2 with Antinociceptive Activity*; Mol Pharmacol 78(2010):560-568). Based on such studies, compounds capable of activating the GPR35 receptors have been considered for application as analgesic drugs and screening of GPR35 activators has been suggested as a method for identifying new analgesic drugs. Therefore, activation of the GPR35 receptor by 6' SL and by LNT provides strong basis for use of compositions comprising such human milk oligosaccharides for the benefit of reducing nociception. The synergistic activator effect of 6' SL and LNT on GPR35 also provides a strong basis for a superior nociceptive effect of such human milk oligosaccharide when used in combination.

Accordingly, the present invention therefore provides a nutritional composition comprising 6'-sialyllactose (6'SL) and lacto-N-tetraose (LNT) for use in a method of reducing nociception in an infant or a young child.

The present invention also provides a growing-up milk comprising 6'-sialyllactose (6' SL) and lacto-N-tetraose (LNT) for use in a method of reducing nociception in a child.

The nutritional composition, respectively the growing up milk, of the present invention is in particular advantageous for use in a method of:
reducing abdominal pain;
reducing pain associated with gastrointestinal discomfort and/or gastrointestinal disorders;
reducing crying periods;
improving the quality of sleep; and
improving the quality of life
in an infant or a young child, respectively in a child.

The invention also relates to the use of
a nutritional composition comprising 6' sialyllactose (6' SL) and lactoNtetraose (LNT) in a method of
reducing crying periods;
improving the quality of sleep; and
improving the quality of life
in an infant or a young child; and
a nutritional composition in the form of a growingup milk comprising 6' sialyllactose (6'SL) and lactoNtetraose (LNT) in a method of
reducing crying periods;
improving the quality of sleep; and
improving the quality of life
in an child.

DETAILED DESCRIPTION

Figure 1:
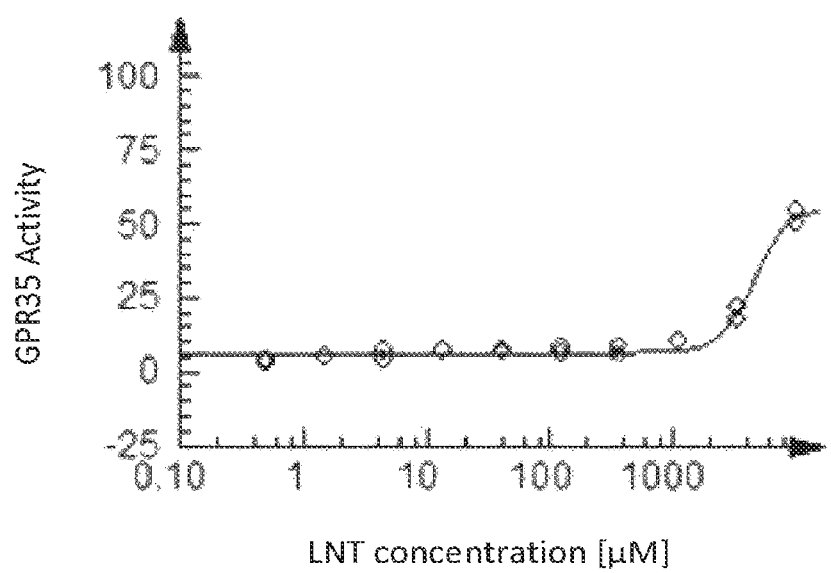
FIG. 1: In vitro response of GPR35 to LNT in the cell based-assay of Example 2. The EC50 value is 4.5 mM.

As used herein, the following terms have the following meanings.

The term "infant" means a child under the age of 12 months. The expression "young child" means a child aged between one and less than three years, also called toddler. The expression "child" means a between three and seven years of age.

An "infant or young child born by C-section" means an infant or young child who was delivered by caesarean. It means that the infant or young child was not vaginally delivered.

An "infant or young child vaginally born" means an infant or young child who was vaginally delivered and not delivered by caesarean.

A "preterm" or "premature" means an infant or young child who was not born at term. Generally it refers to an infant or young child born prior 37 weeks of gestation.

An "infant having a low birth weight" means a new born having a body weight below 2500 g (5.5 pounds) either because of preterm birth or restricted fetal growth. It therefore encompasses:

infant or young child who has/had a body weight from 1500 to 2500 g at birth (usually called "low birth weight" or LBW)

infant or young child who has/had a body weight from 1000 to 1500 g at birth (called "very low birth weight" or VLBW)

infant or young child who has/had a body weight under 1000 g at birth (called "extremely low birth weight" or ELBW).

An "infant born small for gestational age (SGA)" means a baby with birth weights below the 10th percentile for babies of the same gestational age.

The expression "nutritional composition" means a composition which nourishes a subject. This nutritional composition is usually to be taken orally or intravenously, and it usually includes a lipid or fat source and a protein source.

In a particular embodiment the composition of the present invention is a hypoallergenic nutritional composition. The expression "hypoallergenic nutritional composition" means a nutritional composition which is unlikely to cause allergic reactions.

In a particular embodiment the composition of the present invention is a "synthetic nutritional composition". The expression "synthetic nutritional composition" means a mixture obtained by chemical and/or biological means, which can be chemically identical to the mixture naturally occurring in mammalian milks (i.e. the synthetic composition is not breast milk).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The expression "growing-up milk" (or GUM) refers to a milk-based drink generally with added vitamins and minerals, that is intended for young children or children.

The term "fortifier" refers to liquid or solid nutritional compositions suitable for mixing with breast milk or infant formula.

The expression "weaning period" means the period during which the mother's milk is substituted by other food in the diet of an infant or young child.

The expressions "days/weeks/months/years of life" and "days/weeks/months/years of birth" can be used interchangeably.

The expression "reducing nociception" encompasses one or several of the following:

reducing abdominal pain;

reducing pain associated with gastrointestinal discomfort and/or gastrointestinal disorders;

reducing crying periods;

improving the quality of sleep; and improving the quality of life.

The "mother's milk" should be understood as the breast milk or the colostrum of the mother.

An "oligosaccharide" is a saccharide polymer containing a small number (typically three to ten) of simple sugars (monosaccharides).

The term "HMO" or "HMOs" refers to human milk oligosaccharide(s). These carbohydrates are highly resistant to enzymatic hydrolysis, indicating that they may display essential functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "fucosylated oligosaccharide" is an oligosaccharide having a fucose residue. It has a neutral nature. Some examples are 2-FL (2' fucosyllactose), 3-FL (3-fucosyllactose), difucosyllactose, lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyl-lacto-N-neohexaose, difucosyllacto-N-hexaose I, difucosyl-lacto-N-neohexaose II and any combination thereof. Without wishing to be bound by theory it is believed that the fucosyl-epitope of the fucosylated oligosaccharides may act as decoy at the mucosal surface. By a competition effect, it may prevent and/or limit the action of the pathogens responsible of infections (of viral or bacterial origin) or of their secreted components (e.g. toxins), especially by avoiding their binding to natural ligands, and without to be bound by theory, this is believed to therefore reduce the risk of infections/inflammations, and particularly the risk of LRT/ear infections and/or inflammations. In addition, the fucosylated oligosaccharides are thought to boost growth and metabolic activity of specific commensal microbes reducing inflammatory response and creating an environment unfavourable for pathogens thus leading to colonization resistance.

The expressions "fucosylated oligosaccharides comprising a 2'-fucosyl-epitope" and "2-fucosylated oligosaccharides" encompass fucosylated oligosaccharides with a certain homology of form since they contain a 2'-fucosyl-epitope, therefore a certain homology of function can be expected. Without wishing to be bound by theory the 2'-fucosyl-epitope of these fucosylated oligosaccharides is believed to be particularly specific to pathogens (or their secreted components) involved in the LRT and/or ear infections.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose), para-lacto-N-neohexaose (para-LNnH), LNnT (lacto-N-neotetraose) and any combinations thereof. Other examples are lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose.

The expression "at least one fucosylated oligosaccharide" and "at least one N-acetylated oligosaccharide" means "at least one type of fucosylated oligosaccharide" and "at least one type of N-acetylated oligosaccharide".

A "precursor of HMO" is a key compound that intervenes in the manufacture of HMO, such as sialic acid and/or fucose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6' SL (6' sialyllactose).

The nutritional composition of the present invention can be in solid form (e.g. powder) or in liquid form. The amount of the various ingredients (e.g. the oligosaccharides) can be expressed in g/100 g of composition on a dry weight basis when it is in a solid form, e.g. a powder, or as a concentration in g/L of the composition when it refers to a liquid form (this latter also encompasses liquid composition that may be obtained from a powder after reconstitution in a liquid such as milk, water . . . , e.g. a reconstituted infant formula or a follow-on/follow-up formula or a growing-up milk or an infant cereal product or any other formulation designed for infant nutrition).

The term "prebiotic" means non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics.* JNutr. 1995; 125: 1401-12).

The term "probiotic" means microbial cell preparations or components of microbial cells with a beneficial effect on the health or well-being of the host. (Salminen S, Ouwehand A. Benno Y. et al. "*Probiotics: how should they be defined*" Trends Food Sci. Technol. 1999:10 107-10). The microbial cells are generally bacteria or yeasts.

The term "cfu" should be understood as colony-forming unit.

All percentages are by weight unless otherwise stated.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

The invention will now be described in further details. It is noted that the various aspects, features, examples and embodiments described in the present application may be compatible and/or combined together.

A first object of the present invention is therefore a nutritional composition comprising 6'-sialyllactose (6' SL) and lacto-N-tetraose (LNT), for use in reducing nociception in an infant or a young child.

A second object of the present invention is a growing-up milk comprising 6'-sialyllactose (6' SL) and lacto-N-tetraose (LNT), for use in reducing nociception in a child.

To achieve such benefits, the nutritional composition, respectively the growing-up milk, of the invention is preferably for use in a method of reducing abdominal pain in subject;

reducing pain associated with gastrointestinal discomfort and gastrointestinal disorders, wherein gastrointestinal discomfort is preferably caused by colic, bloating and/or cramps and wherein the gastrointestinal disorder is preferably selected from inflammatory bowel disease (IBD), diarrhea, e.g. infectious diarrhea, necrotizing enterocolitis (NEC) and functional abdominal pain disorders, such functional abdominal pain disorders being preferably selected from irritable bowel syndrome (IBS), abdominal migraine and functional abdominal pain—not otherwise specified (FAP-NOS);

reducing crying periods in a subject, preferably reducing crying periods in a subject experiencing pain, preferably in a subject experiencing abdominal pain, most preferably in a subject experiencing pain associated with gastrointestinal discomfort and/or gastrointestinal disorders such as defined above;

improving the quality of sleep in a subject, preferably in a subject experiencing pain, more preferably in a subject experiencing abdominal pain, most preferably in a subject experiencing pain associated with gastrointestinal discomfort and/or gastrointestinal disorders such as defined above; and improving the quality of life of a subject, preferably of a subject experiencing pain, more preferably of a subject experiencing abdominal pain, most preferably in a subject experiencing pain associated with gastrointestinal discomfort and/or gastrointestinal disorders such as defined above.

wherein the subject is an infant or a young child, respectively a child.

For the purpose of the present invention, the reduction of pain is achieved by reducing the perception of pain. The compositions of the present invention have an impact on the mechanism of nociception and are therefore able to reduce the perception of pain irrespective of the origin of such pain. It is therefore effective to reduce for example the perception of pain originating from the performance of a medical or surgical act or from some injury, disease, disorder and/or discomfort. The mechanism of reducing the perception of pain is different from the reduction of pain that can be achieved by treating the injury, disease, disorder or discomfort that is causing the pain. It is therefore intended that the composition of the present invention is not for treating the injury, disease, disorder or discomfort that is causing the pain but only for relieving the subject from the perception of the pain.

In a particularly advantageous embodiment of the present invention, 6' SL and LNT are present in the nutritional composition or the growing-up milk in some particular amounts.

In a preferred embodiment of the invention, LNT is present in the nutritional composition or the growing-up milk in an amount of 0.005-3 g/L of the composition. In some embodiments, LNT may be in an amount of 0.01-1.5 g/L of the composition, such as 0.04-1.2 g/L or 0.05-1 g/L or 0.09-0.8 g/L of the composition. In a particular embodiment, LNT is in an amount of 0.5 g/L of the composition. In another particular embodiment, LNT is in an amount of 0.1 g/L of the composition.

LNT can be present in the nutritional composition or the growing-up milk in an amount of 0.004-2.3 g/100 g of composition on a dry weight basis, LNT may be present in an amount of 0.008-1.2 g/100 g of composition, such as 0.03-0.9 g/100 g or 0.04-0.8 g/100 g or 0.07-0.6 g/100 g of the composition. In a particular embodiment, LNT is present in an amount of 0.38 g/100 g of the composition. In another particular embodiment, LNT is present in an amount of 0.08 g/100 g of the composition.

LNT may be synthesised chemically by enzymatic transfer of saccharide units from donor moieties to acceptor moieties using glycosyltransferases as described for example in U.S. Pat. No. 5,288,637 and WO 96/10086.

In another preferred embodiment of the invention the nutritional composition or the growing-up milk may comprise from 0.005-5 g/L of 6'SL, or from 0.008-2.5 g/L, or from 0.01-1 g/L, or from 0.03-0.7 g/L, for example 0.04 or 0.5 g/L.

The nutritional composition or the growing-up milk according to the invention can contain 0.004-3.8 g of 6'SL per 100 g of composition on a dry weight basis, e.g. 0.006-1.9 g or 0.008-0.8 g or 0.023-0.5 g or 0.031-0.4 g of 6'SL per 100 g of composition on a dry weight basis, for example 0.18 g or 0.04 g per 100 g of composition on a dry weight basis.

6'SL may be isolated by chromatographic or filtration technology from a natural source such as animal milks. Alternatively, it may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. 6'SL formation can be initiated by acceptor substrates starting from any degree of polymerisation (DP), from DP=1 onwards. Alternatively, 6'SL may be produced by chemical synthesis from lactose and free N'-acetylneuraminic acid (sialic acid).

In a particular aspect, the 6'SL and the LNT comprised in the nutritional composition or the growing-up milk according to the invention are typically present in a ratio 6' SL:LNT of from 3:1 to 1:3, such as 2:1 to 1:2 or 2:1 to 1:1. In a particularly advantageous embodiment, this ratio is 2:1 or around 2.1 preferably this ratio is 1:1 or around 1:1.

In a particular aspect of the invention, the nutritional composition or the growing-up milk comprises 6'SL and LNT wherein:

6'SL is in an amount of 0.005-5 g/L of the composition and/or in an amount of 0.004-3.8 g/100 g of composition on a dry weight basis; and/or LNT is in an amount of 0.005-3 g/L of the composition and/or in an amount of 0.004-2.3 g/100 g of composition on a dry weight basis.

In a particular aspect of the invention, the nutritional composition or the growing-up milk comprises 6'SL and LNT wherein:

6'SL is in an amount of 0.008-2.5 g/L of the composition and/or in an amount of 0.006-1.9 g/100 g of composition on a dry weight basis; and/or LNT is in an amount of 0.01-1.5 g/L of the composition and/or in an amount of 0.008-1.2 g/100 g of composition on a dry weight basis.

In another particular embodiment the nutritional composition or the growing-up milk of the present invention comprises 6'SL and LNT wherein:

6'SL is in an amount of 0.01-1 g/L of the composition and/or in an amount of 0.008-0.8 g/100 g of composition on a dry weight basis; and/or LNT is in an amount of 0.04-1.2 g/L of the composition and/or in an amount of 0.03-0.9 g/100 g of composition on a dry weight basis.

In another particular embodiment the nutritional composition or the growing up milk of the present invention comprises 6'SL and LNT wherein:

6' SL is in an amount of 0.03-0.7 g/L of the composition and/or in a total amount of 0.023-0.5 g/100 g of composition on a dry weight basis; and/or LNT is in an amount of 0.05-1 g/L of the composition and/or in an amount of 0.04-0.8 g/100 g of composition on a dry weight basis.

In another particular embodiment the nutritional composition or the growing up milk of the present invention comprises 6'SL and LNT wherein:

6'SL is in an amount of 0.04-0.5 g/L of the composition and/or in an amount of 0.031-0.4 g/100 g of composition on a dry weight basis; and/or LNT is in an amount of 0.09-0.8 g/L of the composition and/or in an amount of 0.07-0.6 g/100 g of composition on a dry weight basis.

In a specific embodiment the nutritional composition or the growing-up milk according to the invention comprises 6'SL and LNT wherein:

6'SL is in an amount of 0.24 or 0.05 g/L of the composition and/or in an amount of 0.18 or 0.04 g/100 g of composition on a dry weight basis; and/or LNT is in an amount of 0.5 g/L or 0.1 g/L of the composition and/or in an amount of 0.38 g/100 g of composition or 0.08 g/100 g of composition on a dry weight basis.

In a particular embodiment, 6'SL is provided in the nutritional composition or growing-up milk of the present invention in such an amount that normal consumption of the nutritional composition or growing-up milk would provide to the infant or young child, respectively the child, consuming it a total daily dose of 0.003 to 6.5 g, preferably 0.005-3.3 g or 0.006-1.3 g or 0.02-0.9 g, for example 0.024-0.7 g per day.

In a particular embodiment, the LNT is provided in the nutritional composition or growing-up milk of the present invention in such an amount that normal consumption of the nutritional composition or growing-up milk would provide to the infant or young child, respectively the child, consuming it a total daily dose of 0.003-3.9 g, preferably 0.006-2 g or 0.02-1.6 g or 0.03-1.3 g, for example 0.05-1 g per day.

In particular embodiments of the present invention, the nutritional composition, respectively the growing-up milk, of the present invention can comprise additional human milk oligosaccharides. Even when such human milk oligosaccharide are not effective in activating the GPR35 receptors, these may be added to address other health benefits.

Therefore, in a particular embodiment, the nutritional composition or the growing-up milk further comprises at least one fucosylated oligosaccharide. There can be one or several types of fucosylated oligosaccharide(s). The fucosylated oligosaccharide(s) can indeed be selected from the list comprising 2'-fucosyllactose, 3' fucosyllactose, difucosyllactose, lacto-N-fucopentaose (such as lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose (such as fucosyllacto-N-neohexaose I, fucosyllacto-N-neohexaose II), difucosyllacto-N-hexaose I, difuco-lacto-N-neohexaose, difucosyllacto-N-neohexaose I, difucosyllacto-N-neohexaose II, fucosyl-para-Lacto-N-hexaose, tri-fuco-para-Lacto-N-hexaose I and any combination thereof.

In some particular embodiments the fucosylated oligosaccharide comprises a 2'-fucosyl-epitope. It can be for example selected from the list comprising 2'-fucosyllactose, difucosyllactose, lacto-N-fucopentaose, lacto-N-fucohexaose, lacto-N-difucohexaose, fucosyllacto-N-hexaose, fucosyllacto-N-neohexaose, difucosyllacto-N-hexaose difuco-lacto-N-neohexaose, difucosyllacto-N-neohexaose, fucosyl-para-Lacto-N-hexaose and any combination thereof.

In a particular embodiment, the nutritional composition, respectively the growing-up milk, according to the invention comprises 2'-fucosyllactose (or 2FL, or 2'FL, or 2-FL or 2'-FL). In a particular embodiment, there is no other type of fucosylated oligosaccharide than 2'-fucosyllactose, i.e. the nutritional composition or growing-up milk of the invention comprises only 2'-fucosyllactose as fucosylated oligosaccharide.

The fucosylated oligosaccharide(s) may be isolated by chromatography or filtration technology from a natural source such as animal milks. Alternatively, it may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

In another particular aspect of the invention, the nutritional composition or the growing-up milk can comprise at least one N-acetylated oligosaccharide in addition to LNT. There can be one or several types of N-acetylated oligosaccharide. In some particular embodiments the N-acetylated oligosaccharide is lacto-N-neotetraose (LNnT), para-lacto-N-neohexaose (para-LNnH) or any combination thereof. In some particular embodiments the N-acetylated oligosaccharide is LNnT. In some particular embodiments where LNnT is present the nutritional composition or the growing-up milk can comprise both LNT and LNnT in a ratio LNT:LNnT between 5:1 and 1:2, or from 2:1 to 1:1, or from 2:1.2 to 2:1.6.

The N-acetylated oligosaccharide(s) may be synthesised chemically by enzymatic transfer of saccharide units from donor moieties to acceptor moieties using glycosyltransferases as described for example in U.S. Pat. No. 5,288,637 and WO 96/10086. Alternatively, LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyllactosamine produced in this way may then be transferred to lactose as the acceptor moiety.

In a particularly advantageous embodiment of the present invention, the nutritional composition or the growing-up milk comprises 2'-fucosyllactose (2FL) and/or lacto-N-neotetraose (LNnT).

In a particular embodiment, the nutritional composition or the growing-up milk according to the invention can comprise other sialylated oligosaccharide(s) in addition to 6' SL, such as 3'-sialyllactose (3-SL).

The sialylated oligosaccharide(s) may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

The nutritional composition or the growing-up milk according to the present invention may also comprise other types of oligosaccharide(s) (i.e. other than human milk oligosaccharides mentioned above) and/or at least a fiber(s) and/or at least a precursor(s) thereof. The other oligosaccharide and/or fiber and/or precursor thereof may be selected from the list comprising galacto-oligosaccharides (GOS), fructo-oligosaccharides (FOS), inulin, xylooligosaccharides (XOS), polydextrose and any combination thereof. They may be in an amount between 0 and 10% by weight of composition. In a particular embodiment, the nutritional composition or the growing-up milk can also contain at least one BMO (bovine milk oligosaccharide).

Suitable commercial products that can be used to prepare the nutritional compositions or the growing-up milk according to the invention include combinations of FOS with inulin such as the product sold by BENEO under the trademark Orafti, or polydextrose sold by Tate & Lyle under the trademark STA-LITE®.

The nutritional composition or the growing-up milk according to the present invention may optionally also comprise at least one precursor of oligosaccharide. There can be one or several precursor(s) of oligosaccharides. For example the precursor of human milk oligosaccharide is sialic acid, fucose or a mixture thereof. In some particular embodiments the composition comprises sialic acid.

In particular examples the nutritional composition or the growing-up milk comprises from 0 to 3 g/L of precursor(s) of oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of oligosaccharide. The composition according to the invention can contain from 0 to 2.1 g of precursor(s) of oligosaccharide per 100 g of composition on a dry weight basis, e.g. from 0 to 1.5 g or from 0 to 0.8 g or from 0 to 0.15 g of precursor(s) of oligosaccharide per 100 g of composition on a dry weight basis.

The nutritional composition or the growing-up milk of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly Bifidobacteria and/or Lactobacilli.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM 1-2116, *Lactobacillus johnsonii* CNCM 1-1225, *Streptococcus salivarius* DSM 13084 sold by BLIS Technologies Limited of New Zealand under the designation KI2, *Bifidobacterium lactis* CNCM 1-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The nutritional composition or the growing-up milk according to the invention may contain from 10e3 to 10e12 cfu of probiotic strain, more preferably between 10e7 and 10e12 cfu such as between 10e8 and 10e10 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments. Probiotic components and metabolites can also be added.

The nutritional composition according to the invention can be for example an infant formula, a starter infant formula, a follow-on or follow-up formula, a growing-up milk, a baby food, an infant cereal composition, a fortifier such as a human milk fortifier, or a supplement. In some particular embodiments, the composition of the invention is an infant formula, a fortifier or a supplement that may be intended for the first 4 or 6 months of age. In a preferred embodiment the nutritional composition of the invention is an infant formula.

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses. In such cases it is particularly useful to define the amount of N-acetylated oligosaccharides and optionally other oligosaccharides in terms or daily dose to be administered to the infant or young child, such as described above.

The nutritional composition of the present invention can be in solid (e.g. powder), liquid or gelatinous form. In a specific embodiment the nutritional composition is a supplement comprising 6' SL and LNT in a ratio of 1:3 to 3:1, wherein the supplement is in powder form and provided in a sachet, preferably a sachet with 1 to 10 g of the mixture of 6' SL and LNT per sachet, or in the form of a syrup, preferably a syrup with a total solid concentration of 5 to 75 g/100 mL (5 to 75% (w/v)). When the supplement is in powder form, it may comprise a carrier. It is however preferred that the supplement is devoid of a carrier. When the supplement is in the form of a syrup, the HMOs are preferably dissolved or suspended in water acidified with citrate.

The nutritional composition or the growing-up milk according to the invention generally contains a protein source. The protein can be in an amount of from 1.6 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids. The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

The protein component can alternatively be replaced by a mixture or synthetic amino acid, for example for preterm or low birth weight infants.

In a particular embodiment the nutritional composition or the growing-up milk according to the invention is a hypoallergenic composition. In another particular embodiment the composition according to the invention is a hypoallergenic nutritional composition or growing-up milk.

The nutritional composition or the growing-up milk according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

The nutritional composition or the growing-up milk according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, structured triglyceride oil, high oleic sunflower oil and high oleic safflower oil, medium-chain-triglyceride oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n–6 to n–3 fatty acids of about 5:1 to about 15:1; for example about 8:1 to about 10:1.

The nutritional composition or the growing-up milk of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B 1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition or the growing-up milk of the invention may contain emulsifiers and stabilisers such as soy, lecithin, citric acid esters of mono- and diglycerides, and the like.

The nutritional composition or the growing-up milk of the invention may also contain other substances which may have a beneficial effect such as lactoferrin, nucleotides, nucleosides, and the like.

The nutritional composition or the growing-up milk of the invention may also contain carotenoid(s). In some particular embodiments of the invention, the nutritional composition of the invention does not comprise any carotenoid.

The nutritional composition or the growing-up milk according to the invention may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

The fucosylated oligosaccharide(s) and the N-acetylated oligosaccharide(s) may be added at this stage, especially if the final product is to have a liquid form. If the final product is to be a powder, they may likewise be added at this stage if desired.

The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 301 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The fucosylated oligosaccharide(s) and the N-acetylated oligosaccharide(s) may also or alternatively be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement. The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The nutritional composition according to the invention is for use in infants or young children. The infants or young children may be born term or preterm. In a particular embodiment the nutritional composition of the invention is for use in infants or young children that were born preterm, having a low birth weight and/or born small for gestational age (SGA). In a particular embodiment the nutritional composition of the invention is for use in preterm infants, infants having a low birth weight and/or infants born small for gestational age (SGA).

The nutritional composition of the present invention may also be used in an infant or a young child that was born by C-section or that was vaginally delivered.

In some embodiments the composition according to the invention can be for use before and/or during the weaning period.

The nutritional composition can be administered (or given or fed) at an age and for a period that depends on the needs.

The nutritional composition can be for example given immediately after birth of the infants. The composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some particularly advantageous embodiments of the invention, the nutritional composition is given (or administered) to an infant within the first 4, 6 or 12 months of birth of said infant. In some other embodiments, the nutritional composition of the invention is given few days (e.g. 1, 2, 3, 5, 10, 15, 20 . . . ), or few weeks (e.g. 1, 2, 3, 4, 5, 6, 7, 8, 9, 10 . . . ), or few months (e.g. 1, 2, 3, 4, 5, 6, 7, 8, 9, 10 . . . ) after birth. This may be especially the case when the infant is premature, but not necessarily.

In one embodiment the composition of the invention is given to the infant or young child as a supplementary composition to the mother's milk. In some embodiments the infant or young child receives the mother's milk during at least the first 2 weeks, first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the 1st, 2nd or 4th month of life, during at least 1, 2, 4 or 6 months.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on/follow-up formula.

EXAMPLES

The following examples illustrate some specific embodiments of the composition for use according to the present invention. The examples are given solely for the purpose of illustration and are not to be construed as limitations of the present invention.

Example 1

An example of the composition of a nutritional composition (e.g. an infant formula) according to the present invention is given in the below table 1. This composition is given by way of illustration only.

TABLE 1

Composition of the infant formula of Example 1

| Nutrients | | per 100 kcal | per litre |
|---|---|---|---|
| Energy (kcal) | | 100 | 670 |
| Protein (g) | | 1.83 | 12.3 |
| Fat (g) | | 5.3 | 35.7 |
| Linoleic acid (g) | | 0.79 | 5.3 |
| α-Linolenic acid (mg) | | 101 | 675 |
| Lactose (g) | | 11.2 | 74.7 |
| Minerals (g) | | 0.37 | 2.5 |
| Na (mg) | | 23 | 150 |
| K (mg) | | 89 | 590 |
| Cl (mg) | | 64 | 430 |
| Ca (mg) | | 62 | 410 |
| P (mg) | | 31 | 210 |
| Mg (mg) | | 7 | 50 |
| Mn (µg) | | 8 | 50 |
| Se (µg) | | 2 | 13 |
| Vitamin A (µg RE) | | 105 | 700 |
| Vitamin D (us) | | 1.5 | 10 |
| Vitamin E (mg TE) | | 0.8 | 5.4 |
| Vitamin K1 (µg) | | 8 | 54 |
| Vitamin C (mg) | | 10 | 67 |
| Vitamin B1 (mg) | | 0.07 | 0.47 |
| Vitamin B2 (mg) | | 0.15 | 1.0 |
| Niacin (mg) | | 1 | 6.7 |
| Vitamin B6 (mg) | | 0.075 | 0.50 |
| Folic acid (µg) | | 9 | 60 |
| Pantothenic acid (mg) | | 0.45 | 3 |
| Vitamin B12 (µg) | | 0.3 | 2 |
| Biotin (µg) | | 2.2 | 15 |
| Choline (mg) | | 10 | 67 |
| Fe (mg) | | 1.2 | 8 |
| I (µg) | | 15 | 100 |
| Cu (mg) | | 0.06 | 0.4 |
| Zn (mg) | | 0.75 | 5 |
| Oligosaccharides | 6'SL (g) | 0.035 | 0.24 |
| (HMOs) | LNT (g) | 0.07 | 0.45 |

Example 2

Principle of the Assay

Six human milk oligosaccharides (LNnT, LNT, 2-FL, diFL, 6' SL and 3-SL) were sreened for their ability to activate the GPR35 receptor in an in vitro assay. The screening was conducted by DiscoverX (Fremont, Ca, USA) using the PathHunter (β-Arresin assay. This assay monitors the activation of GPR35 expressed in cultured cells, using Enzyme Fragment Complementation with (β-galactosidase ((β-Gal) as the functional reporter. The enzyme is split into two inactive complementary portions, EA and PK, expressed as fusion proteins in the cell. EA is fused to (β-Arrestin and PK is fused to GPR35. When the GPR35 is activated and (β-Arrestin is recruited to the receptor, PK and EA complementation occurs, restoring (β-Gal activity, which is measured using chemiluminescent Detection Reagents.

Methods

The GPR35 cell line was expanded from frozen stocks and cultured according to standard procedures. Cells were seeded in a total volume of 20 µL into white walled, 384-well microplates and incubated at 37° C. for the appropriate time prior to testing. All testing was done in duplicate.

HMO samples were shipped to DiscoverX as concentrated stocks in Phosphate Buffered saline. On the test day, a 5x compound working intermediate was prepared in PBS. Five µL of 5x sample was added to cells and incubated at room temperature for 3 to 5 hours.

Assay signal was generated through a single addition of 12.5 µL (50% v/v) of PathHunter Detection reagent cocktail, followed by one-hour incubation at room temperature. Microplates were read following signal generation with a PerkinElmer Envision™ instrument for chemiluminescent signal detection.

Zaprinast (which is known to be an activator of GPR35) was used as positive control.

Percentage activity was calculated using the following formula:

% Activity=100%×(mean RLU of test sample−mean RLU of vehicle control)/(mean MAX control ligand−mean RLU of vehicle control).

Dose-responses were generated by iterative 3x dilutions of the highest concentration tested (10 mM).

Findings

Figure 2:
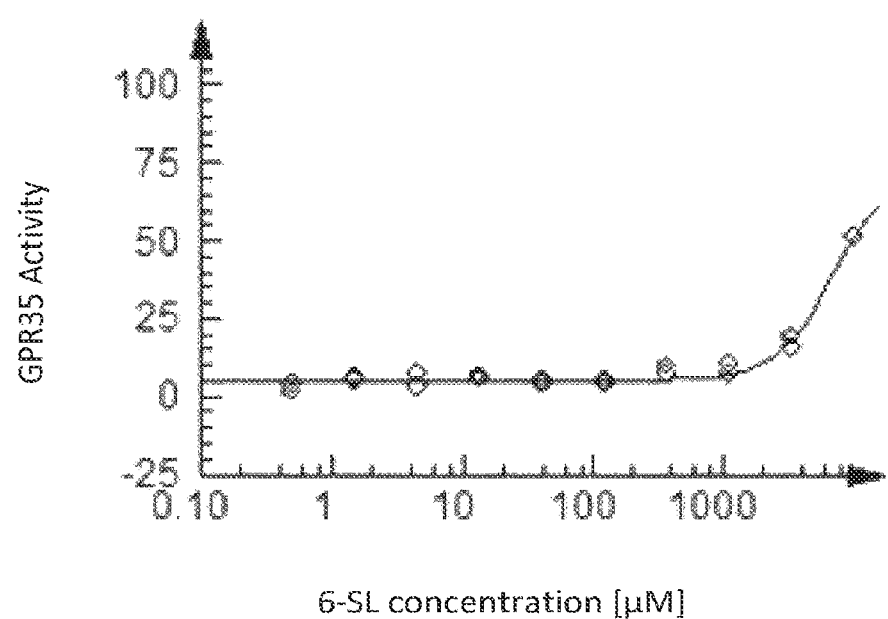
FIG. 2: In vitro response of GPR35 to 6'SL in the cell based-assay of Example 2. The EC50 value is 6.5 mM.

LNT activated GPR35 with an EC50 of 4.5 mM (FIG. 1). 6'SL activated GPR35 with an EC50 of 6.5 mM (FIG. 2). No activation of GPR35 was obtained with 3SL, 2FL, diFL and LNnT.

Figure 3:
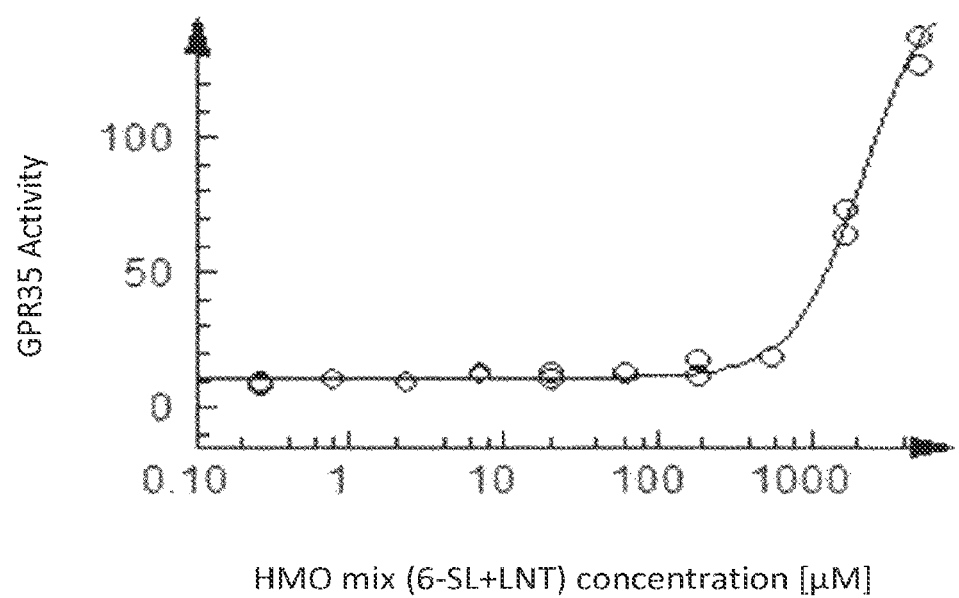
FIG. 3: In vitro response of GPR35 to HMO mix consisting of a mixture of 6'SL and LNT in the cell based-assay of Example 2. The EC50 value is 2.2 mM.
Figure 4A:
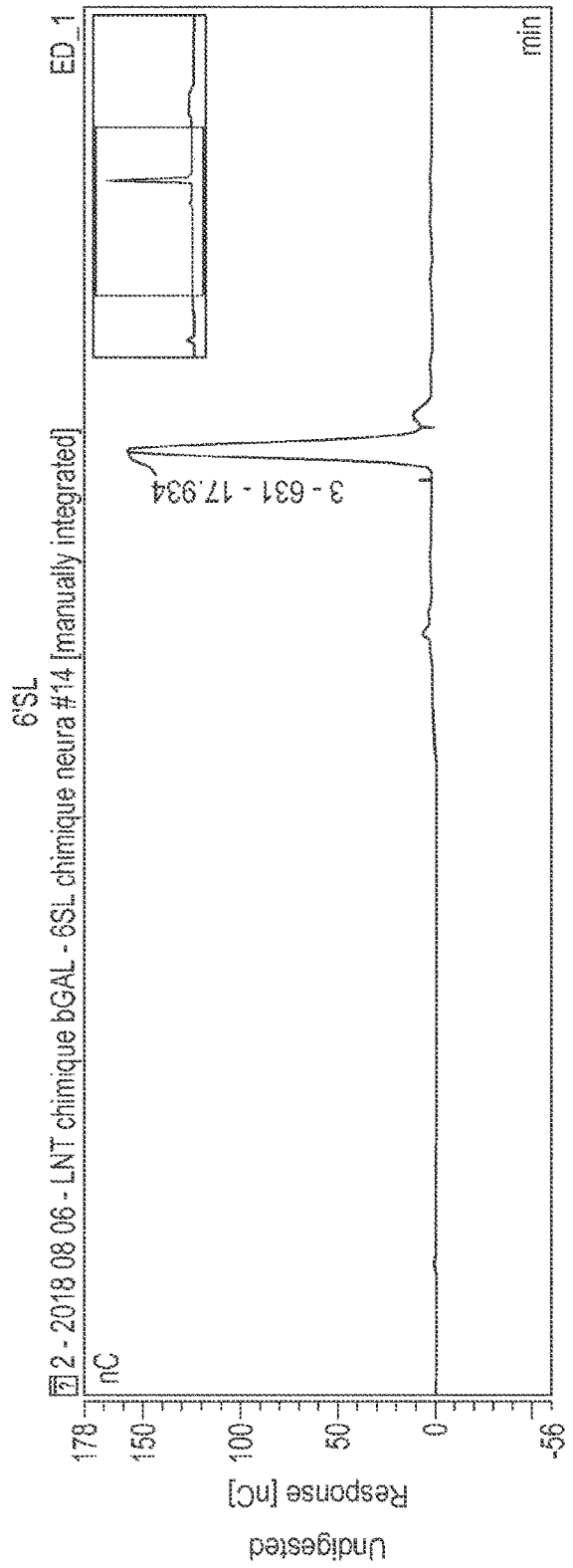
FIG. 4A: HPAEC/PAD analysis of 6' SL before and after treatment with Neuraminidase (6'SL) or β-galactosidase (LNT) showing complete digestion of both HMOs.
Figure 4B:
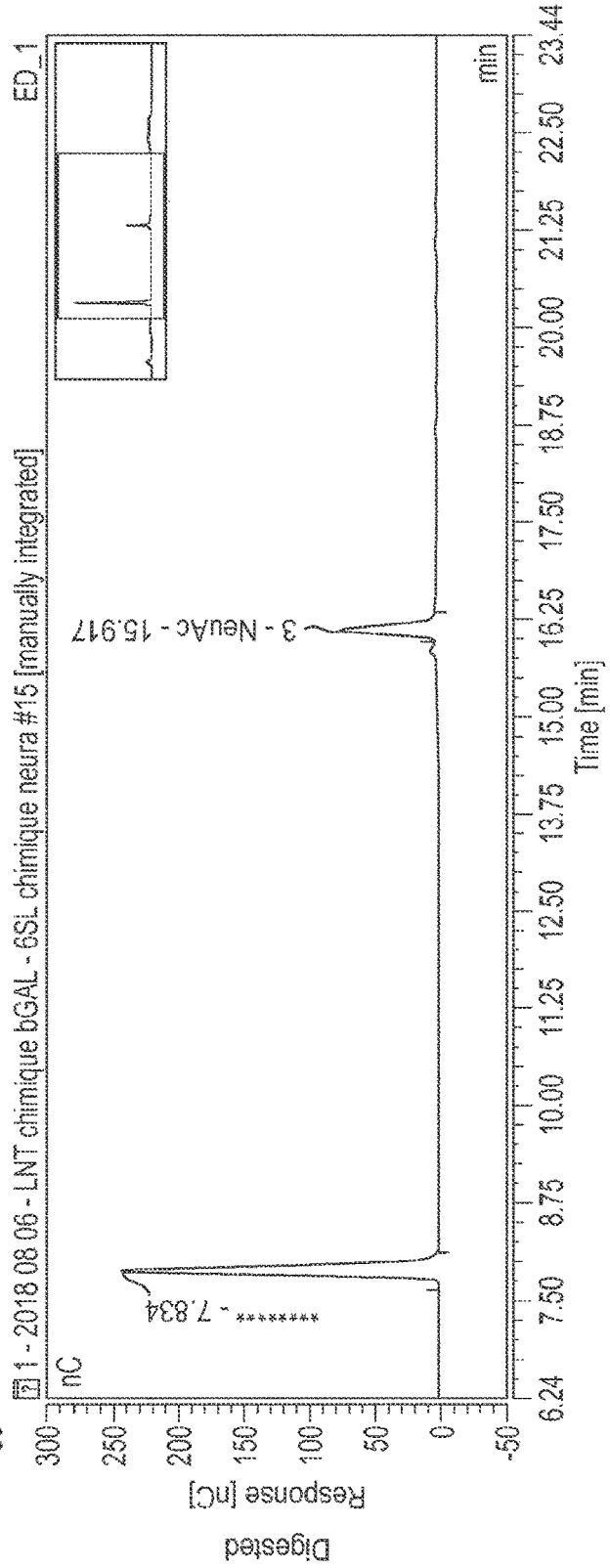
FIG. 4B: HPAEC/PAD analysis of 6' SL before and after treatment with Neuraminidase (6'SL) or β-galactosidase (LNT) showing complete digestion of both HMOs.
Figures 4C, 4D:
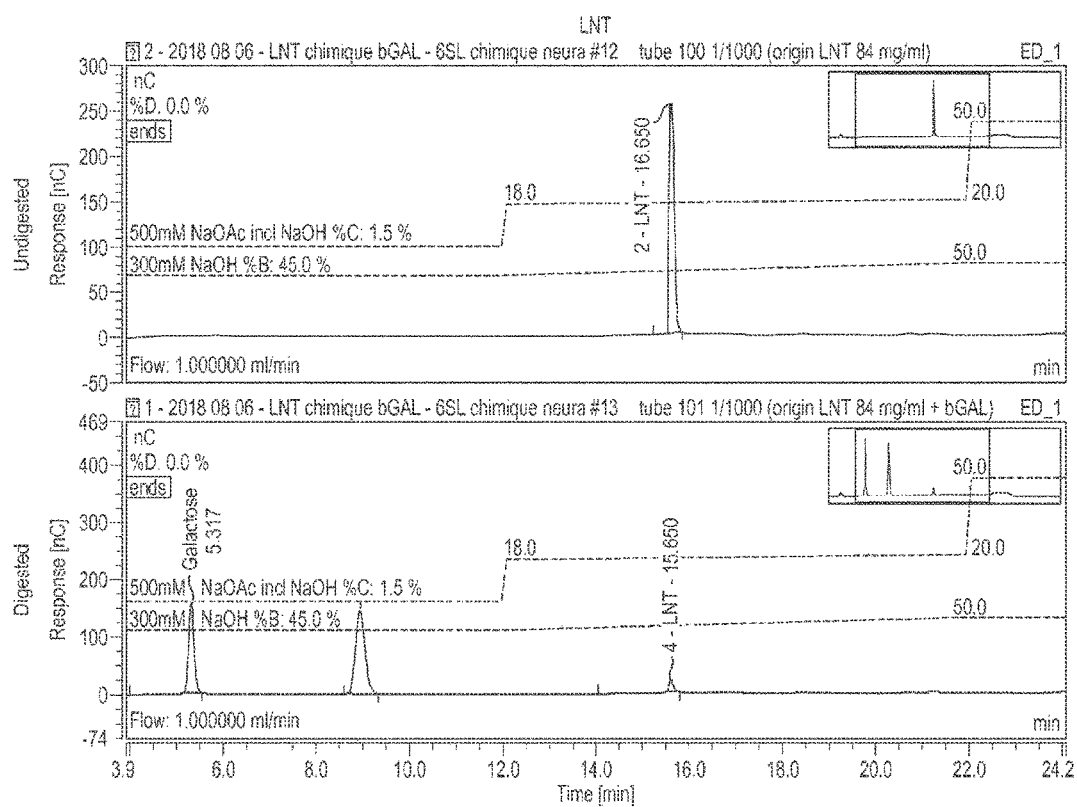
FIG. 4C: HPAEC/PAD analysis of LNT before and after treatment with Neuraminidase (6'SL) or β-galactosidase (LNT) showing complete digestion of both HMOs.
FIG. 4D: HPAEC/PAD analysis of LNT before and after treatment with Neuraminidase (6'SL) or β-galactosidase (LNT) showing complete digestion of both HMOs.

As LNT and 6' SL were found as being activators, these two HMOs were tested in combination. An equimolar mix of 6'SL and LNT activated GPR35 with an EC50 of 2.2 mM (FIG. 3). These results demonstrate a synergy between 6' SL and LNT.

A mixture of all six HMOs at an equimolar ratio was also tested, showing similar results as with the combination of LNT and 6' SL. These results demonstrate that the synergistic effect of LNT and 6' SL is maintained even when admixed with other human milk oligosaccharides.

Example 3

The following trials were done by digesting LNT and 6' SL and using the digested material to run the GPR35 activation assay, such as to validate the results of the trial of Example 2.

Digestion of Lnt by β-Galactosidase

LNT was digested by 3-galactosidase purified from *Aspergillus niger* (Megazyme, ref: E-AGLAN) using the following protocol: in a 1.5 ml screw cap tube with external thread, we mixed 84 mg of LNT in 900 µL of 100 mM acetate buffer (pH 4.5) and 100 µL of enzyme (400 U). This tube was incubated for 72 h at 55° C. in a ThermoMix shaker with 450 rpm shaking. The inactivation of the enzyme was done by heat treatment of 5 minutes at 100° C. The inactivated tube was stored at −20° C. until further analysis.

Digestion of 6'SL by Neuraminidase

6' SL was digested by neuraminidase purified from *Clostridium perfringens* (Megazyme, ref: E-SIALCP) using the following protocol: in a 1.5 ml screw cap tube with external thread, we mixed 78 mg of 6' SL in 900 11.1 of 50 mM phosphate buffer (pH 6.0) and 50 µL of enzyme (50 U). This tube was incubated for 72 h at 37° C. in a ThermoMix shaker with 450 rpm shaking. The inactivation of the enzyme was done by heat treatment of 5 minutes at 100° C. The inactivated tube was stored at −20° C. until further analysis.

Control of the Digestions

We confirmed that the digestions of LNT and 6' SL were complete by quantifying them using High Performance Anion Exchange Chromatography equipped with pulse amperometric detection (HPAEC-PAD). The results of the analysis are provided in FIGS. 4A-4D. Peaks clearly confirm complete digestion of both LNT and 6' SL.

Preparation of Samples, Sample Tests and Results

Figure 5:
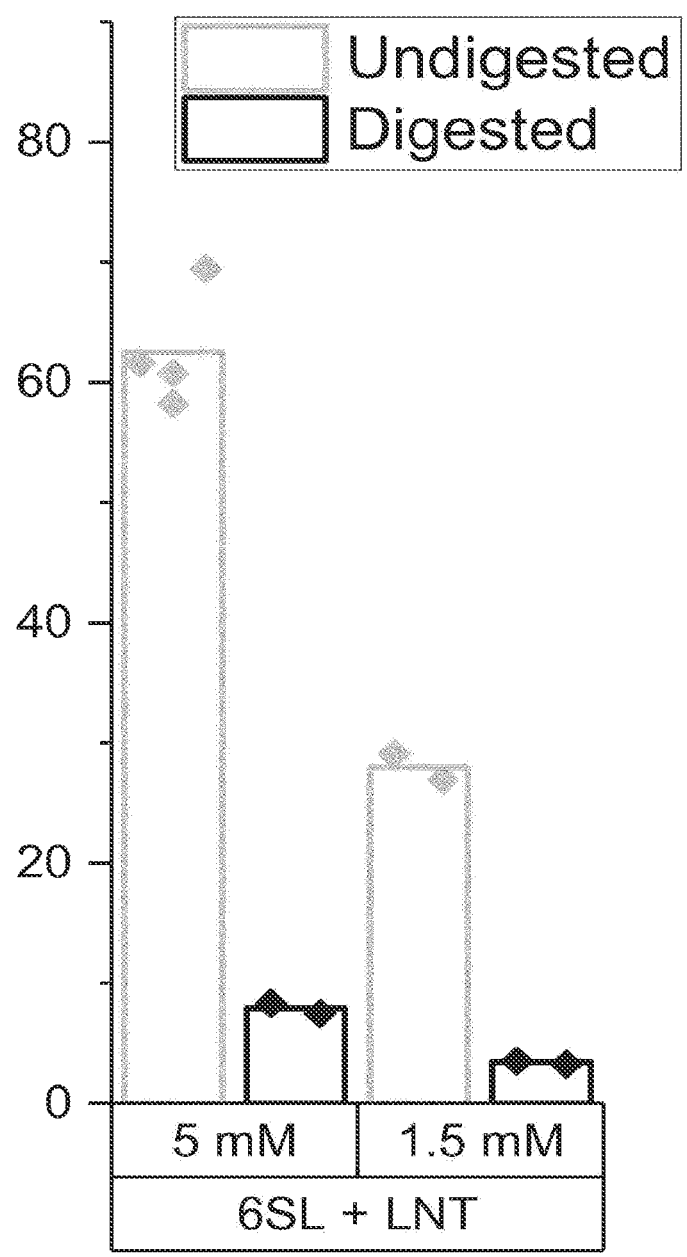
FIG. 5: In vitro response of GPR35 to HMO mix consisting of a mixture of 6'SL and LNT in the cell based assay of Example 2 (bars hashed with horizontal lines) compared with a mix of digested 6' SL and LNT (bars hashed with vertical lines). The graph shows that activity is activation of the receptor is lost when 6' SL and LNT are digested.

The samples were diluted in 1xPBS (pH ~7) at 5x concentrations and sent to DiscoverX. The GPR35 activation assay was performed as described in Example 2. The results are provided in FIG. 5. Response of GPR35 to digested and undigested mix of LNT and 6'SL showed a response with the undigested mix and background response to the digested mix, thereby demonstrating the specificity of the GPR35 response to LNT and 6'SL.

Example 4

The effectiveness of a combination of 6'SL and LNT in reducing nociception was confirmed in vivo.

Water Avoidance Stress (WAS) and Nutritional Interventions

C57B1.6/J mice were purchased from Janvier SA (Le Genest St. Isle, France). Upon their arrival, they were kept in polypropylene cages in a temperature-controlled room with a 12-hour dark-light cycle during 1 week before electrodes implantation (see below). Five days after surgery, mice were submitted to daily WAS by placing them individually 1 h during 9 days on a 3x3 cm platform in a 40x40 cm size pool filled with cold tap water up to 1 cm from the top of the platform. Sham WAS consisted of placing the animals for 1 h/day on the platform in a waterless pool. Animals have free access to water and food. Specific diets were started 3 days before WAS procedure and continued until the end of experiment. Three groups of 12 mice were randomly assigned to the following nutritional interventions:

Group 1: Control diet (AIN93), sham WAS (non sensitized)
Group 2: Control diet (was:AIN93), WAS (sensitized)
Group 3: Experimental diet (WAS:LNT+6'SL), AIN93 supplemented with 6' SL 0.09% w/v and LNT 0.18% w/v), WAS (sensitized)

Colorectal Distension (CRD)

To measure abdominal contractions as an index of pain, mice were equipped with 2 nickel-chrome wire electrodes implanted into the abdominal external oblique muscle and one under the skin of the abdomen. Surgery was performed under xylazine/ketamine anesthesia (both 1.2 mg, subcutaneously). A small ballon (Fogarty, Edwards Laboratories Inc., Santa Anna, USA) was introduced in the rectum and fixed at the base of the tail. The balloon was progressively inflated from 0 to 0.10 ml, by steps of 0.02 ml. Each step of distension lasted 10 sec alternated with a 5 min recovery period in between without distension.

Visceral sensitivity to CRD was assessed by abdominal muscle electromyography

Results

Figure 6:
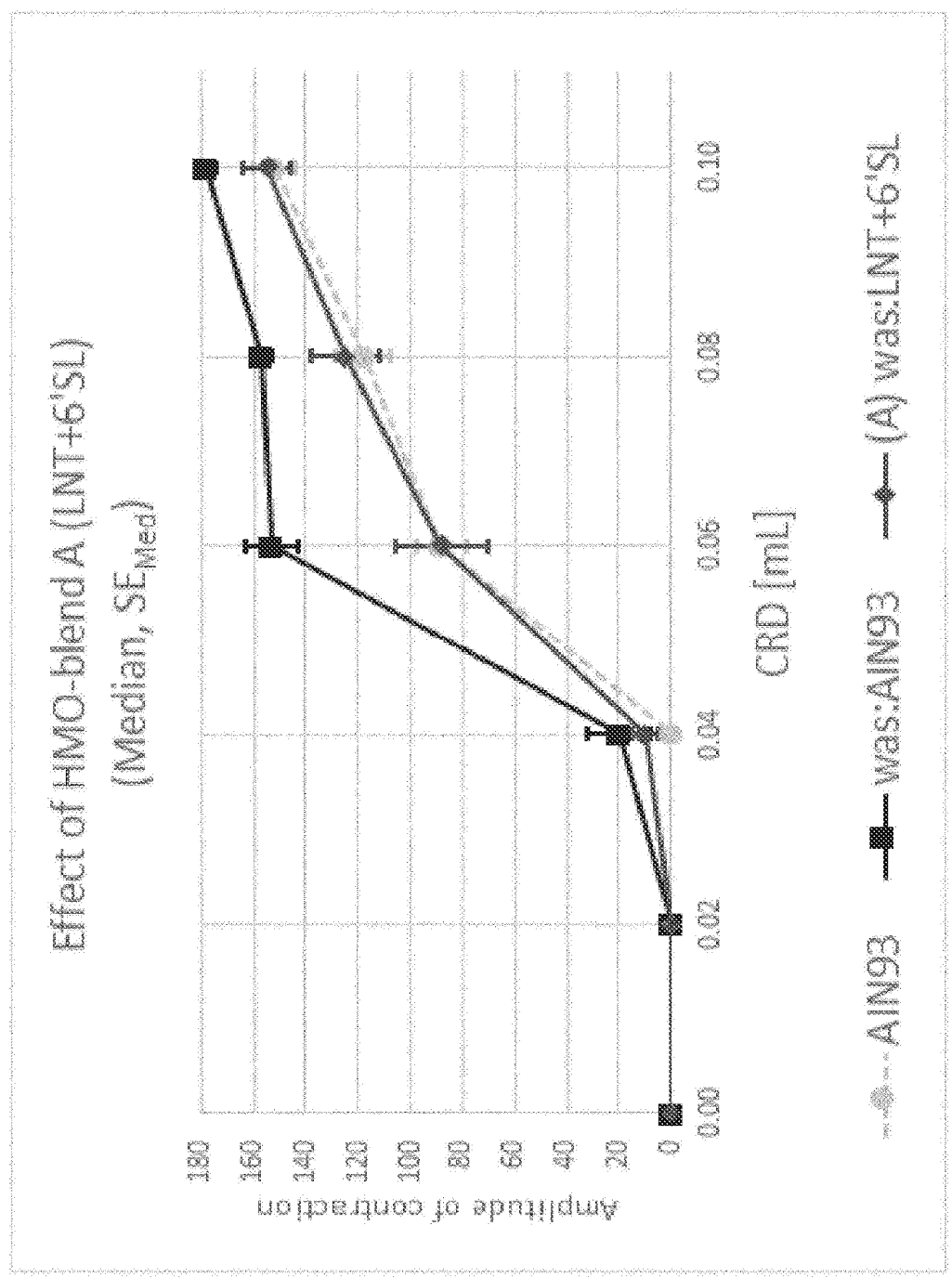
FIG. 6: amplitude of contraction measured as a function of colorectal dilatation in non-sensitized mice (AIN93; dots), in sensitized mice (was:AIN93; squares) and in sensitized mice to which 6'SL and LNT have been administered (was:LNT+6'SL; diamonds).

The results are provided in FIG. 6. The amplitude of contraction, which is associated with pain perceived by the mice, was significantly increased by the fact that WAS mice were sensitized (was:AIN93, Group 2), compared to non-sensitized mice (AIN93, Group 1). Administration of a blend of 6' SL and LNT was able to reduce the amplitude of contraction and thus the perceived pain of sensitized mice (was:LNT+6'SL, Group 3). For a CRD of 0.06 mL and above, the amplitude of contraction can even not be statistically distinguished from what is observed in non-sensitized mice. This is a very relevant achievement because a CRD of 0.06 mL corresponds to the typical threshold of pain, whereas smaller dilatation volumes are rather associated with discomfort.

The invention claimed is:

1. A method for reducing nociception in a child in need thereof, the method comprising administering to the child a growing-up milk comprising 6'-sialyllactose (6'SL) and lacto-N-tetraose (LNT), wherein the growing-up milk does not include any fucosylated oligosaccharide.

2. The method according to claim 1, wherein the growing-up milk is administered in an effective amount for reducing abdominal pain in the child.

3. The method according to claim 1, wherein the growing-up milk is administered in an effective amount for reducing pain associated with gastrointestinal discomfort and/or with a gastrointestinal disorder.

4. The method according to claim 1, wherein the growing-up milk is administered in an effective amount for reducing crying periods in the child.

5. The method according to claim 1, wherein the growing-up milk is administered in an effective amount for improving the quality of sleep in the child.

6. The method according to claim 1, wherein the growing-up milk is administered in an effective amount for improving the quality of life in the child.

7. The method according to claim 1, wherein the child experiences abdominal pain.

8. The method according to claim 1, wherein the child experiences pain associated with gastrointestinal discomfort and/or gastrointestinal disorder.

9. The method according to claim 1, wherein the growing-up milk further comprises at least one probiotic in an amount of from 103 to 1012 cfu/g of the growing-up milk by dry weight.

10. The method according to claim 1, wherein the 6'SL and the LNT are present in a weight ratio 6' SL:LNT from 3:1 to 1:3.

11. The method according to claim 1, wherein the 6'SL is present in an amount of 0.005 to 5 g/L or 0.004 to 3.8 g/100 g of the growing-up milk on a dry weight basis.

12. The method according to claim 1, wherein the LNT is present in an amount of 0.005-3 g/L or 0.004-2.3 g/100 g of the growing-up milk on a dry weight basis.

13. The method according to claim 1, wherein:
  a. the 6'SL is in an amount of 0.005-5 g/L of the growing-up milk and/or in an amount of 0.004-3.8 g/100 g of the growing-up milk on a dry weight basis; and/or
  b. the LNT is in an amount of 0.005-3 g/L of the growing-up milk and/or in an amount of 0.004-2.3 g/100 g of the growing-up milk on a dry weight basis.

14. The method according to claim 1, wherein:
  a. the 6'SL is in an amount of 0.008-2.5 g/L of the growing-up milk and/or in an amount of 0.006-1.9 g/100 g of the growing-up milk on a dry weight basis; and/or
  b. the LNT is in an amount of 0.01-1.5 g/L of the growing-up milk and/or in an amount of 0.008-1.2 g/100 g of the growing-up milk on a dry weight basis.

15. The method according to claim 1, wherein:
  a. the 6'SL is in an amount of 0.01-1 g/L of the growing-up milk and/or in an amount of 0.008-0.8 g/100 g of the growing-up milk on a dry weight basis; and/or
  b. the LNT is in an amount of 0.04-1.2 g/L of the growing-up milk and/or in an amount of 0.03-0.9 g/100 g of the growing-up milk on a dry weight basis.

16. The method according to claim 1, wherein:
  a. the 6'SL is in an amount of 0.03-0.7 g/L of the growing-up milk and/or in a total amount of 0.023-0.5 g/100 g of the growing-up milk on a dry weight basis; and/or
  b. the LNT is in an amount of 0.05-1 g/L of the growing-up milk and/or in an amount of 0.04-0.8 g/100 g of the growing-up milk on a dry weight basis.

17. The method according to claim 1, wherein:
  a. the 6'SL is in an amount of 0.04-0.5 g/L of the growing-up milk and/or in an amount of 0.031-0.4 g/100 g of the growing-up milk on a dry weight basis; and/or
  b. the LNT is in an amount of 0.09-0.8 g/L of the growing-up milk and/or in an amount of 0.07-0.6 g/100 g of the growing-up milk on a dry weight basis.

18. The method according to claim 1, wherein the growing-up milk further comprises at least one additional ingredient selected from the group consisting of N-acetylated oligosaccharides, sialylated oligosaccharides, galacto-oligosaccharides (GOS), fructo-oligosaccharides (FOS), xylooligosaccharides (XOS), inulin, polydextrose, sialic acid, fucose and any combination thereof.

19. The method according to claim 1, wherein the child has inflammatory bowel disease (IBD).

* * * * *